US00PP17446P2

(12) United States Plant Patent
van Ostaayen

(10) Patent No.: US PP17,446 P2
(45) Date of Patent: Feb. 27, 2007

(54) *HYPERICUM* PLANT NAMED 'AUTUMN SURPRISE'

(50) Latin Name: *Hypericum×inodorum*
Varietal Denomination: Autumn Surprise

(75) Inventor: Cornelis Petrus Maria van Ostaayen, Zundert (NL)

(73) Assignee: Witteman + Co., Hillegom (NL)

( * ) Notice: Subject to any disclaimer, the term of this patent is extended or adjusted under 35 U.S.C. 154(b) by 27 days.

(21) Appl. No.: 11/151,836

(22) Filed: Jun. 14, 2005

(51) Int. Cl.
*A01H 5/00* (2006.01)

(52) U.S. Cl. ..... Plt./226
(58) Field of Classification Search ..... Plt./226, Plt./263
See application file for complete search history.

(56) References Cited

PUBLICATIONS

UPOV–ROM GTITM Plant Variety Database, 2006/01, GTI Jouve Retrieval Software, Citation for *Hypericum* 'Autumn Surprise', one page.*

* cited by examiner

*Primary Examiner*—Kent Bell
*Assistant Examiner*—June Hwu
(74) *Attorney, Agent, or Firm*—C. A. Whealy

(57) ABSTRACT

A new and distinct cultivar of *Hypericum* plant named 'Autumn Surprise', characterized by its upright and outwardly spreading plant habit; freely branching growth habit; and tri-colored variegated leaves.

1 Drawing Sheet

Botanical designation: *Hypericum×inodorum.*
Cultivar denomination: 'Autumn Surprise'.

BACKGROUND OF THE INVENTION

The present Invention relates to a new and distinct cultivar of *Hypericum* plant, botanically known as *Hypericum×inodorum*, and hereinafter referred to by the name 'Autumn Surprise'.

The new *Hypericum* is a naturally-occurring branch mutation of an unnamed selection of *Hypericum×inodorum*, not patented. The new *Hypericum* was discovered and selected by the Inventor in 1999 from within a population of plants of the parent selection in a controlled environment in Boskoop, The Netherlands.

Asexual reproduction of the new *Hypericum* by terminal cuttings in Zundet, The Netherlands since 2000, has shown that the unique features of this new *Hypericum* are stable and reproduced true to type in successive generations of asexual reproduction.

SUMMARY OF THE INVENTION

The following traits have been repeatedly observed and are determined to be the unique characteristics of 'Autumn Surprise'. These characteristics in combination distinguish 'Autumn Surprise' as a new and distinct cultivar:

1. Upright and outwardly spreading plant habit.
2. Freely branching growth habit.
3. Variegated leaves.

Plants of the new *Hypericum* differ from plants of the parent selection primarily in leaf coloration as plants of the parent selection do not have variegated leaves.

Plants of the new *Hypericum* can be compared to plants of the *Hypericum* cultivar Bosapin, disclosed in U.S. Plant Pat. No. 10,993. In side-by-side comparisons conducted in Boskoop, The Netherlands, plants of the new *Hypericum* differed from plants of the cultivar Bosapin in the following characteristics:

1. Plants of the new *Hypericum* had variegated leaves whereas plants of the cultivar Bosapin had light green-colored leaves.
2. Plants of the new *Hypericum* did not produce flowers whereas plants of the cultivar Bosapin produce flowers and showy fruits.

BRIEF DESCRIPTION OF THE PHOTOGRAPHS

The accompanying colored photographs illustrate the overall appearance of the new *Hypericum*, showing the colors as true as it is reasonably possible to obtain in colored reproductions of this type. Colors in the photographs may differ slightly from the color values cited in the detailed botanical description which accurately describe the colors of the new *Hypericum.*

The photograph at the top of the sheet comprises a side perspective view of a typical plant of 'Autumn Surprise' grown in a container.

The photographs at the middle and at the bottom of the sheet are close-up views of typical leaves of 'Autumn Surprise'.

DETAILED BOTANICAL DESCRIPTION

The new *Hypericum* has not been observed under all possible environmental conditions. The phenotype may vary somewhat with variations in environment such as temperature, daylength and light intensity, without, however, any variance in genotype.

The aforementioned photographs, following observations and measurements describe plants grown in Boskoop, The Netherlands, in an outdoor nursery and under commercial production practices. Plants were about one year old. The photographs and description were taken in September, 2004, when outdoor day temperatures ranged from 16 to 32° C. and night temperatures ranged from 8 to 18° C. In the following description, color references are made to The Royal Horticultural Society Colour Chart, 2001 Edition, except where general terms of ordinary dictionary significance are used.

Botanical classification: *Hypericum×inodorum* cultivar Autumn Surprise.

Parentage: Naturally-occurring branch mutation of an unnamed selection of *Hypericum×inodorum*, not patented.

Propagation:

*Type.*—By cuttings.

*Time to initiate roots.*—About 20 days at 20° C.

*Time to produce a rooted cutting.*—About 50 days at 20° C.

*Root description.*—Fine, fibrous; greyish cream in color.

*Rooting habit.*—Freely branching; dense.

Plant description:

*Plant form.*—Upright and outwardly spreading perennial deciduous shrub; broad inverted triangle.

*Growth habit.*—Moderately vigorous. Freely branching, about 11 lateral branches develop per plant.

*Plant height.*—About 29 cm.

*Plant width* (*spread*).—About 31 cm.

*Lateral branches.*—Length: About 21 cm. Diameter: About 2 mm. Internode length: About 2.7 cm. Strength: Moderately strong. Texture: Smooth; glabrous. Color: 178B.

*Foliage description.*—Arrangement: Opposite, simple; sessile. Length: About 5.8 cm. Width: About 2.4 cm. Shape: Ovate. Apex: Acute to obtuse. Base: Obtuse. Margin: Entire. Texture, upper and lower surfaces: Glabrous, smooth; relatively thick and slightly leathery. Venation pattern: Pinnate. Color: Developing leaves, upper surface: 143A; towards the margins, marbled 145D and 157A. Developing leaves, lower surface: Between 138B and 191A; towards the margin, slightly marbled, 157A and 186D. Fully expanded leaves, upper surface: 137A to 137B; towards the margin, marbled, 138B and 191A; random splashes of 185D and 186A to 186B. Fully expanded leaves, lower surface: Between 138B and 191A; towards the margin, marbled, 145A and 186B. Venation, upper surface: Similar to lamina. Venation, lower surface: 144B.

Flower description: Flower development has not been observed.

Disease/pest resistance: Plants of the new *Hypericum* have not been observed to be resistant to pathogens and pests common to *Hypericum.*

Temperature tolerance: Plants of the new *Hypericum* have been observed to tolerate temperatures ranging from about −15 to 35° C.

It is claimed:

1. A new and distinct cultivar of *Hypericum* plant named 'Autumn Surprise', as illustrated and described.

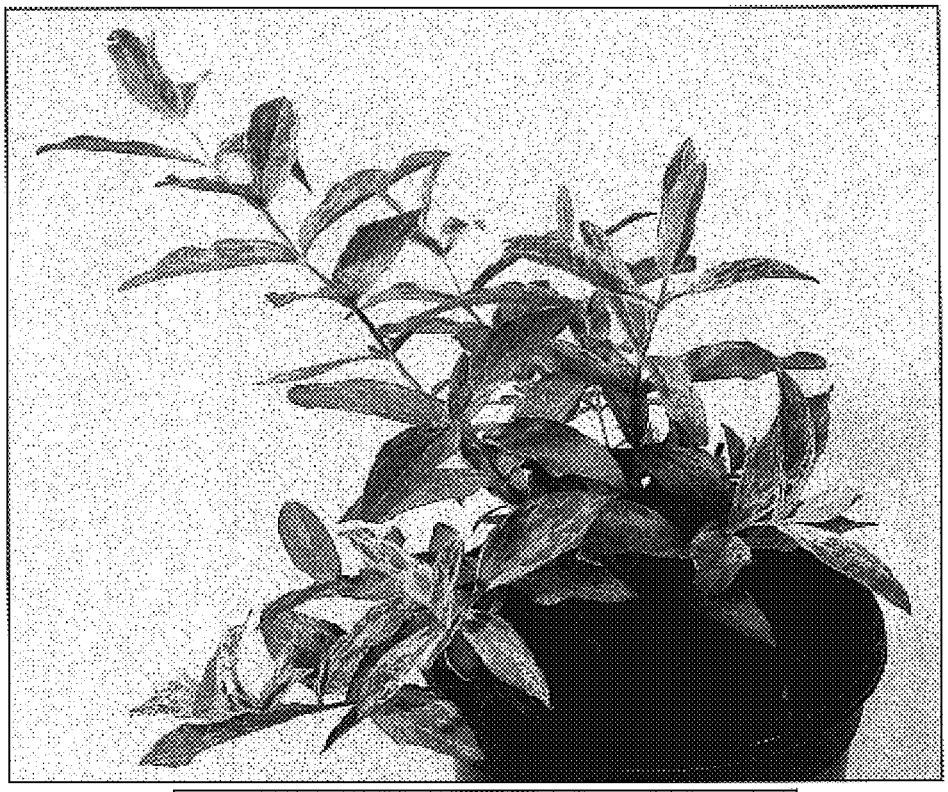
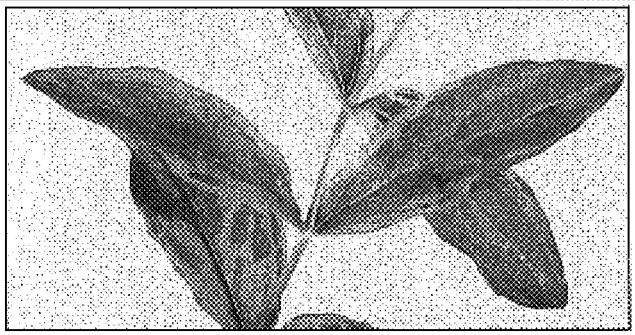
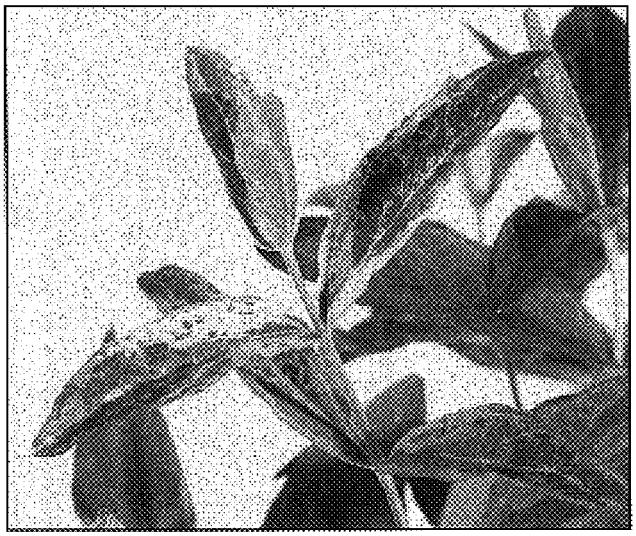

* * * * *